US009384545B2

(12) United States Patent
Uehara et al.

(10) Patent No.: US 9,384,545 B2
(45) Date of Patent: Jul. 5, 2016

(54) X-RAY IMAGE DIAGNOSIS APPARATUS (71) Applicants: Hisayuki Uehara, Otawara (JP); Toshiya Waku, Yaita (JP); Mitsuru Sakata, Yaita (JP); Yoshiyasu Hayashi, Nasushiobara (JP)

(72) Inventors: Hisayuki Uehara, Otawara (JP); Toshiya Waku, Yaita (JP); Mitsuru Sakata, Yaita (JP); Yoshiyasu Hayashi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 538 days.

(21) Appl. No.: 13/687,625

(22) Filed: Nov. 28, 2012

(65) Prior Publication Data
US 2013/0136332 A1 May 30, 2013

(30) Foreign Application Priority Data

Nov. 29, 2011 (JP) ................. 2011-259929

(51) Int. Cl.
*G06K 9/00* (2006.01)
*G06T 7/00* (2006.01)
*A61B 6/00* (2006.01)
*G06T 11/00* (2006.01)

(52) U.S. Cl.
CPC ............ *G06T 7/0012* (2013.01); *A61B 6/4441* (2013.01); *A61B 6/469* (2013.01); *A61B 6/487* (2013.01); *A61B 6/50* (2013.01); *A61B 6/5235* (2013.01); *G06T 11/00* (2013.01); *A61B 6/541* (2013.01)

(58) Field of Classification Search
CPC ..... A61B 6/469; A61B 6/5235; G06T 7/0012
USPC ........................................................ 382/128
See application file for complete search history.

(56) References Cited

U.S. PATENT DOCUMENTS 5,253,169 A * 10/1993 Corby, Jr. ................. 600/431
5,282,254 A * 1/1994 Chiu ..................... G06T 7/004
378/159

(Continued)

FOREIGN PATENT DOCUMENTS

JP          8-164130        6/1996
JP       2004-337423 A     12/2004
JP       2007-159913 A      6/2007

OTHER PUBLICATIONS

Combined Office Action and Search Report issued Jun. 5, 2014 in Chinese Patent Application No. 201210497505.4 (with English translation of category of cited documents).

(Continued)

*Primary Examiner* — Gandhi Thirugnanam
(74) *Attorney, Agent, or Firm* — Oblon, McClelland, Maier & Neustadt, L.L.P.

(57) ABSTRACT

An X-ray image diagnosis apparatus according to an embodiment includes: an image processing unit configured to create a synthesized image by synthesizing an X-ray image of a region of interest inside a given region and an X-ray image of a peripheral region excluding the region of interest in the given region, wherein when the region of interest is changed, the image processing unit acquires an X-ray image of a changed region which is in the region of interest before the change and is changed to the peripheral region, from the X-ray image of the region of interest before the change, and then superimposes the X-ray image of the changed region on the X-ray image of the peripheral region to create the synthesized image.

4 Claims, 5 Drawing Sheets

(56) References Cited

U.S. PATENT DOCUMENTS

| | | | | |
|---|---|---|---|---|
| 5,433,198 A * | 7/1995 | Desai | | 600/374 |
| 5,657,402 A * | 8/1997 | Bender | | G06T 3/4038 |
| | | | | 348/218.1 |
| 6,470,207 B1 * | 10/2002 | Simon et al. | | 600/426 |
| 7,340,033 B2 * | 3/2008 | Mollus et al. | | 378/62 |
| 8,175,357 B2 * | 5/2012 | Ozawa | | 382/130 |
| 8,488,853 B2 * | 7/2013 | Sato et al. | | 382/128 |
| 2001/0043731 A1 * | 11/2001 | Ito | | H04N 1/00127 |
| | | | | 382/132 |
| 2002/0154737 A1 * | 10/2002 | Klotz | | G06T 11/005 |
| | | | | 378/98.12 |
| 2004/0151358 A1 * | 8/2004 | Yanagita et al. | | 382/132 |
| 2005/0277830 A1 * | 12/2005 | Ichihara | | 600/425 |
| 2006/0203966 A1 * | 9/2006 | Mollus | | A61B 6/06 |
| | | | | 378/150 |
| 2006/0241402 A1 * | 10/2006 | Ichihara et al. | | 600/425 |
| 2007/0071296 A1 * | 3/2007 | Nonaka | | A61B 6/486 |
| | | | | 382/128 |
| 2007/0183569 A1 * | 8/2007 | Boese et al. | | 378/62 |
| 2008/0095422 A1 * | 4/2008 | Suri | | G06K 9/6206 |
| | | | | 382/131 |
| 2008/0118115 A1 * | 5/2008 | Williamson | | 382/128 |
| 2008/0187205 A1 * | 8/2008 | Shiozawa | | A61B 6/08 |
| | | | | 382/132 |
| 2009/0163815 A1 * | 6/2009 | Kawagishi et al. | | 600/453 |
| 2009/0274271 A1 * | 11/2009 | Pfister | | A61B 6/12 |
| | | | | 378/62 |
| 2010/0189328 A1 * | 7/2010 | Boernert | | G01R 33/56375 |
| | | | | 382/131 |
| 2010/0220909 A1 * | 9/2010 | Thielemans | | G06T 11/005 |
| | | | | 382/131 |
| 2011/0188726 A1 * | 8/2011 | Nathaniel | | G01N 23/04 |
| | | | | 382/132 |
| 2011/0293164 A1 * | 12/2011 | Sato | | A61B 6/5264 |
| | | | | 382/132 |
| 2013/0063485 A1 * | 3/2013 | Kita | | H04N 5/23232 |
| | | | | 345/629 |
| 2013/0101084 A1 * | 4/2013 | Shimizu | | 378/42 |
| 2013/0136332 A1 * | 5/2013 | Uehara et al. | | 382/132 |
| 2013/0223587 A1 * | 8/2013 | Moriyasu | | A61B 6/03 |
| | | | | 378/5 |
| 2013/0343631 A1 * | 12/2013 | Florent et al. | | 382/132 |

OTHER PUBLICATIONS

Office Action issued Aug. 11, 2015, in Japanese Patent Application No. 2011-259929.

* cited by examiner

X-RAY IMAGE DIAGNOSIS APPARATUS

CROSS-REFERENCE TO THE RELATED APPLICATION

This application is based on and claims the benefit of priority from Japanese Patent Application No. 2011-259929, filed on Nov. 29, 2011; the entire contents of which are incorporated herein by reference.

FIELD

Embodiments described herein relate generally to an X-ray image diagnosis apparatus.

BACKGROUND

X-ray image diagnosis apparatuses are apparatuses which obtain an X-ray image of a subject such as a patient by irradiating the subject with X rays by means of an X-ray irradiator and detecting the X rays having passed through the subject by means of an X-ray detector. As these X-ray image diagnosis apparatuses, an X-ray image diagnosis apparatus has been developed which, for example, includes a C arm configured to hold the X-ray irradiator and the X-ray detector in a mutually facing state and the like, moves the X-ray irradiator and the X-ray detector to an imaging position relative to the subject on a top panel to capture an X-ray image of a target part of the subject, and displays the X-ray image on a monitor.

Such an X-ray image diagnosis apparatus operates in a normal imaging mode and also in an X-ray irradiation mode which may be called a fluoroscopy mode that involves continuous application of a small amount of X rays from the X-ray irradiator and continuous display of X-ray images of the subject. The fluoroscopy mode has often been utilized to locate a target part or to observe a moving part in a moving image. Using the fluoroscopy mode can reduce the amount of X-ray irradiation of the subject and therefore reduce the exposure dose of the subject. Note that X-ray images captured in the fluoroscopy mode are generally called fluoroscopic images.

While reduction in the exposure of the subject is achieved as described above, further reduction in the exposure is desired. In this respect, techniques (e.g. spot imaging method and the like) have been proposed which involve: setting a region of interest (ROI) in a fluoroscopic image (still image) stored in advance; irradiating only the set region of interest with X rays to obtain fluoroscopic images (moving image) of the region of interest; and superimposing the moving image on the still image and displaying them. These techniques have been used, for example, when ablation using a catheter is performed, or in some other similar situation.

However, in the techniques that create a synthesized image by superimposing a moving image on a still image as described above, there is a time difference between the still image stored in advance and the moving image in terms of the timing to capture the image. Thus, the positional relationship of the subject relative to the still image and that relative to the moving image may become different upon body movement of the patient, or the subject, or the like. This may possibly make the synthesized image invalid. To solve this, the region of interest is changed in response to movement of the subject. This, however, requires the still image stored in advance to be changed at the same time. Without doing so, the positional relationship between the region of interest and its peripheral region becomes inaccurate, thereby making it impossible to accurately figure out their positional relationship. Moreover, changing the still image stored in advance requires re-capturing a fluoroscopic image of the peripheral region. This increases the exposure dose and also deteriorates the operability.

DETAILED DESCRIPTION

According one embodiment, an X-ray image diagnosis apparatus includes: an imaging unit configured to capture an X-ray image of a given region of a target part of a subject in a case of obtaining a still image of the target part, and to sequentially capture an X-ray image of a region of interest inside the given region in a case of obtaining a moving image of the target part; an image storage unit configured to store the X-ray image of the given region captured by the imaging unit; an image processing unit configured to create a synthesized image by synthesizing the X-ray image of the region of interest captured by the imaging unit and an X-ray image of a peripheral region excluding the region of interest in the X-ray image of the given region stored in the image storage unit; and a display unit configured to display the synthesized image created by the image processing unit. Moreover, when the region of interest is changed, the image processing unit acquires an X-ray image of a changed region which is in the region of interest before the change and is changed to the peripheral region, from the X-ray image of the region of interest before the change, and then superimposes the X-ray image of the changed region on the X-ray image of the peripheral region to create the synthesized image.

Various Embodiments will be described hereinafter with reference to the accompanying drawings.

First Embodiment

A first embodiment will be described with reference to FIGS. 1 to 4.

Figure 1:
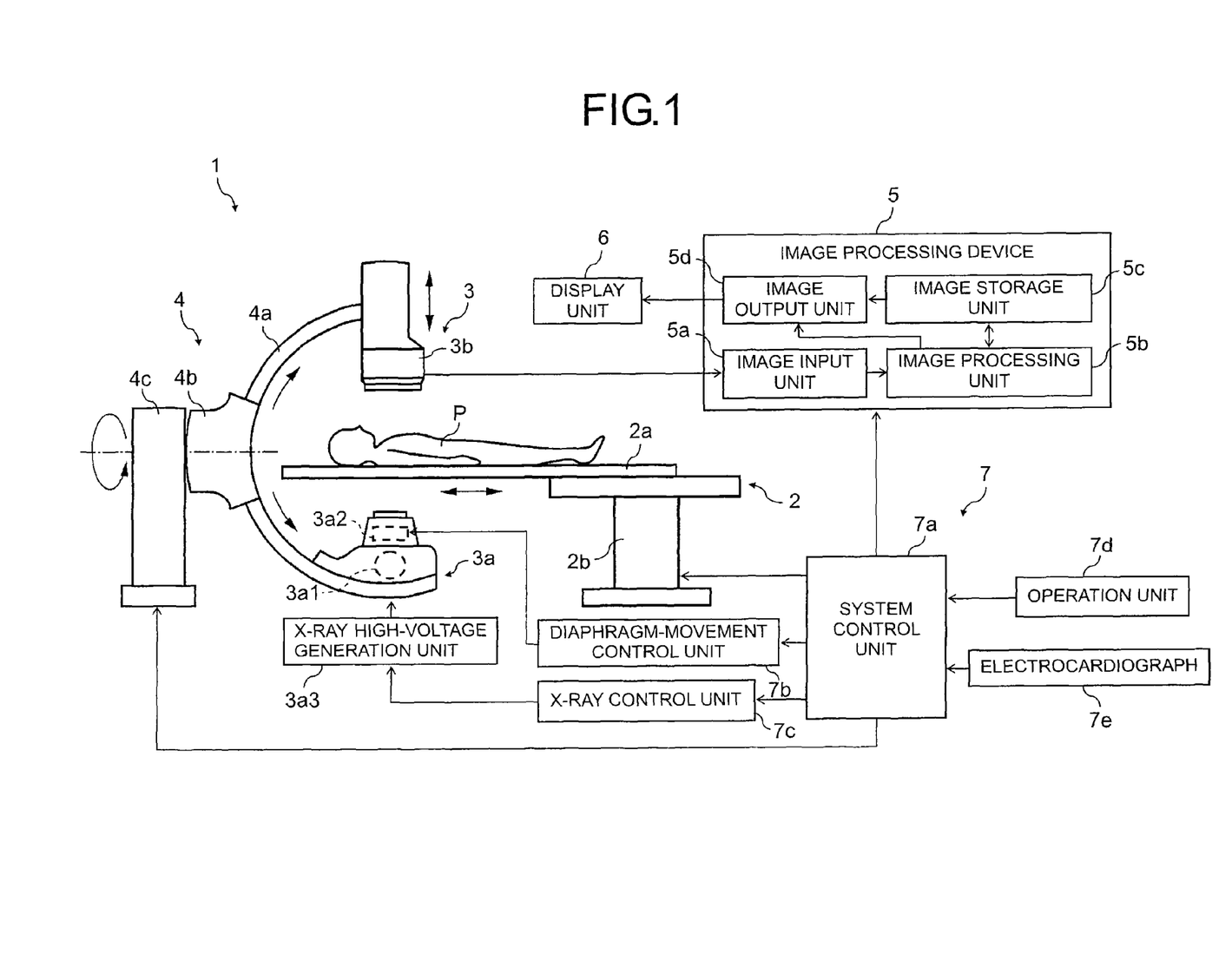
FIG. 1 is a diagram showing a schematic configuration of an X-ray image diagnosis apparatus according to a first embodiment.

As shown in FIG. 1, an X-ray image diagnosis apparatus 1 according to the first embodiment includes: a bed 2 on which to lay a subject P such as a patient; an imaging unit 3 configured to image the subject P on the bed 2; a moving device 4 configured to hold and move the imaging unit 3 to an imaging position; an image processing device 5 configured to process X-ray images; a display unit 6 configured to display various images such as X-ray images; and a control device 7 configured to control each part.

The bed 2 includes a rectangular top panel 2a on which to lay the subject P, and a top-panel drive unit 2b configured to support and move the top panel 2a horizontally and vertically. The top-panel drive unit 2b includes a moving mechanism configured to move the top panel 2a, a drive source configured to supply drive power for this movement, and the like. The bed 2 moves the subject P on the top panel 2a to a desired position by causing the top-panel drive unit 2b to move the top panel 2a to a desired height and also move the top panel 2a horizontally.

The imaging unit 3 includes an X-ray irradiation unit 3a configured to irradiate the subject P on the top panel 2a with X rays, and an X-ray detection unit 3b configured to detect the X rays having passed through the subject P. Being provided movable around the top panel 2a, the imaging unit 3 moves to an imaging position and captures an X-ray image of a target part of the subject P on the top panel 2a from the imaging position. As this X-ray image, a fluoroscopic image of a blood vessel or the like in the target part is captured, for example.

The X-ray irradiation unit 3a includes: an X-ray tube 3a1 configured to emit X rays; a variable X-ray diaphragm 3a2 configured to focus the X rays emitted from the X-ray tube 3a1 to limit the irradiation field (irradiation range) of the X rays; an X-ray high-voltage generation unit 3a3 configured to generate a high voltage to be supplied to the X-ray tube 3a1; and so on. This X-ray irradiation unit 3a irradiates the subject P on the top panel 2a with X rays by causing the X-ray high-voltage generation unit 3a3 to supply a high voltage to the X-ray tube 3a1, causing the X-ray tube 3a1 to emit X rays, and further causing the variable X-ray diaphragm 3a2 to focus the X rays.

Here, various types of variable X-ray diaphragms are available as the variable X-ray diaphragm 3a2. For example, it is possible to use a variable X-ray diaphragm in which four X-ray shield members made of lead or the like are assembled in a parallel crosses shape and which changes the position and size of a window formed and surrounded by the X-ray shield members by moving the X-ray shield members toward or away from each other. That window portion serves as a passage area that allows passage of X rays, while the X-ray shield members outside the window serve as a shield area that absorbs and shields the X rays.

The X-ray detection unit 3b is provided to the moving device 4 in such a way as to face the X-ray tube 3a1 and is formed movable toward and away from the facing X-ray tube 3a1. This X-ray detection unit 3b is electrically connected to the image processing device 5 and transmits the X rays it detects, i.e. X-ray image signals to the image processing device 5. For the X-ray detection unit 3b, an image intensifier, an X-ray flat panel detector (FPD), and the like are available, for example.

The moving device 4 includes: a holding arm 4a configured to hold the X-ray tube 3a1 and the X-ray detection 3b in such postures as to make them face each other; an arm support 4b configured to support the holding arm 4a slidably movably; and a support column 4c configured to support the arm support 4b rotatably.

The holding arm 4a is a C arm in the shape of C, for example, and provided to the arm support 4b slidably movably in the direction the arm extends. At both longitudinal ends of this holding arm 4a, the X-ray tube 3a1 and the X-ray detection unit 3b are provided in the facing postures. Moreover, the arm support 4b holds the holding arm 4a slidably movably and is provided to the support column 4c rotatably. The support column 4c supports the arm support 4b rotatably and is provided standing on a floor surface.

The image processing device 5 includes: an image input unit 5a to which X-ray image signals are inputted; an image processing unit 5b configured to create an X-ray image on the basis of the inputted X-ray image signals; an image storage unit 5c configured to store the created X-ray image; and an image output unit 5d configured to output the created X-ray image or the stored X-ray image to the display unit 6.

The image input unit 5a receives the X-ray image signals detected by the X-ray detection unit 3b and transmits the received X-ray image signals to the image processing unit 5b. The image processing unit 5b creates an X-ray image of the subject P on the basis of the X-ray image signals transmitted from the image input unit 5a and transmits the created X-ray image to the image storage unit 5c or to the image output unit 5d. The image storage unit 5c stores the X-ray image transmitted from the image processing unit 5b. For the image storage unit 5c, a magnetic disk device, a semiconductor disk device (flash memory), and the like are available, for example. The image output unit 5d outputs the X-ray image transmitted from the image processing unit 5b or the X-ray image stored in the image storage unit 5c to the display unit 6.

This image processing device 5 may be configured by hardware such as an electric circuit, or by software such as a program which performs each unit's function, or by a combination of both.

The display unit 6 is a display device configured to display various images such as the X-ray image transmitted from the image output unit 5d. For the display unit 6, a liquid crystal display, a cathode ray tube (CRT) display, and the like are available, for example.

The control device 7 includes: a system control unit 7a configured to control each part of the system; a diaphragm-movement control unit 7b configured to control the variable X-ray diaphragm 3a2; an X-ray control unit 7c configured to control the X-ray high-voltage generation unit 3a3; and an operation unit 7d with which the operator performs input operations. Note that an electrocardiograph 7e configured to record the electrical activity of the heart is connected to the system control unit 7a through a connection line such as a cable.

The system control unit 7a is configured to control each part on the basis of various kinds of programs and data stored. Specifically, the system control unit 7a controls the bed 2, the imaging unit 3, the moving device 4, and so on in accordance with the operator's input operations on the operation unit 7d. Moreover, the system control unit 7a outputs an instruction to execute image processing to the image processing unit 5b of the image processing device 5. The image processing unit 5b executes necessary image processing in response. Note that the system control unit 7a is capable of obtaining information on the position of the holding arm 4a on the basis of an output value from an encoder provided to a drive unit (e.g. servomotor) of the moving device 4 or the like.

The diaphragm-movement control unit 7b controls the opening degree of the variable X-ray diaphragm 3a2 under control of the system control unit 7a. For example, in a case of obtaining a still image of a target part of the subject P, the diaphragm-movement control unit 7b sets the opening degree of the variable X-ray diaphragm 3a2 to an opening degree for capturing an X-ray image of a given region of the target part. Moreover, in a case of obtaining a moving image of the target part, the diaphragm-movement control unit 7b sets the opening degree of the variable X-ray diaphragm 3a2 to an opening degree for capturing X-ray images of a region of interest inside the given region mentioned above (a region smaller than the given region). Note that the diaphragm-movement control unit 7b is capable of obtaining information on the opening degree of the variable X-ray diaphragm 3a2 on the basis of an output value from an encoder provided to a drive unit (e.g. servomotor) of the variable X-ray diaphragm 3a2 or the like.

In order for the X-ray tube 3a1 of the X-ray irradiation unit 3a to generate desired X rays, the X-ray control unit 7c controls various conditions such as the amplitude and pulse width, or the waveform, of the voltage to be given to the X-ray high-voltage generation unit 3a3, under control of the system control unit 7a. This control causes the X-ray high-voltage generation unit 3a3 to raise and rectify voltage and supply that voltage to the X-ray tube 3a1.

The operation unit 7d is an input unit configured to receive input operations from the operator such as a surgeon or an assistant. For this operation unit 7d, input devices such as a joystick, a keyboard, a mouse, and a foot switch are available, for example. The operator such as a surgeon or an assistant performs input operations through the operation unit 7d to move the imaging unit 3 to a desired imaging position.

The electrocardiograph 7e is equipment for recording changes in electricity controlling the movement of the heart and inputs the recorded electrocardiographic waveforms to the system control unit 7a. From the electrocardiographic waveforms, the system control unit 7a can figure out a particular phase (e.g. the end diastole, the end systole, or the like) and can therefore perform imaging at a timing corresponding to that particular phase.

Next, an image synthesizing process performed by the above-described image processing device 5 will be described.

Figure 2:
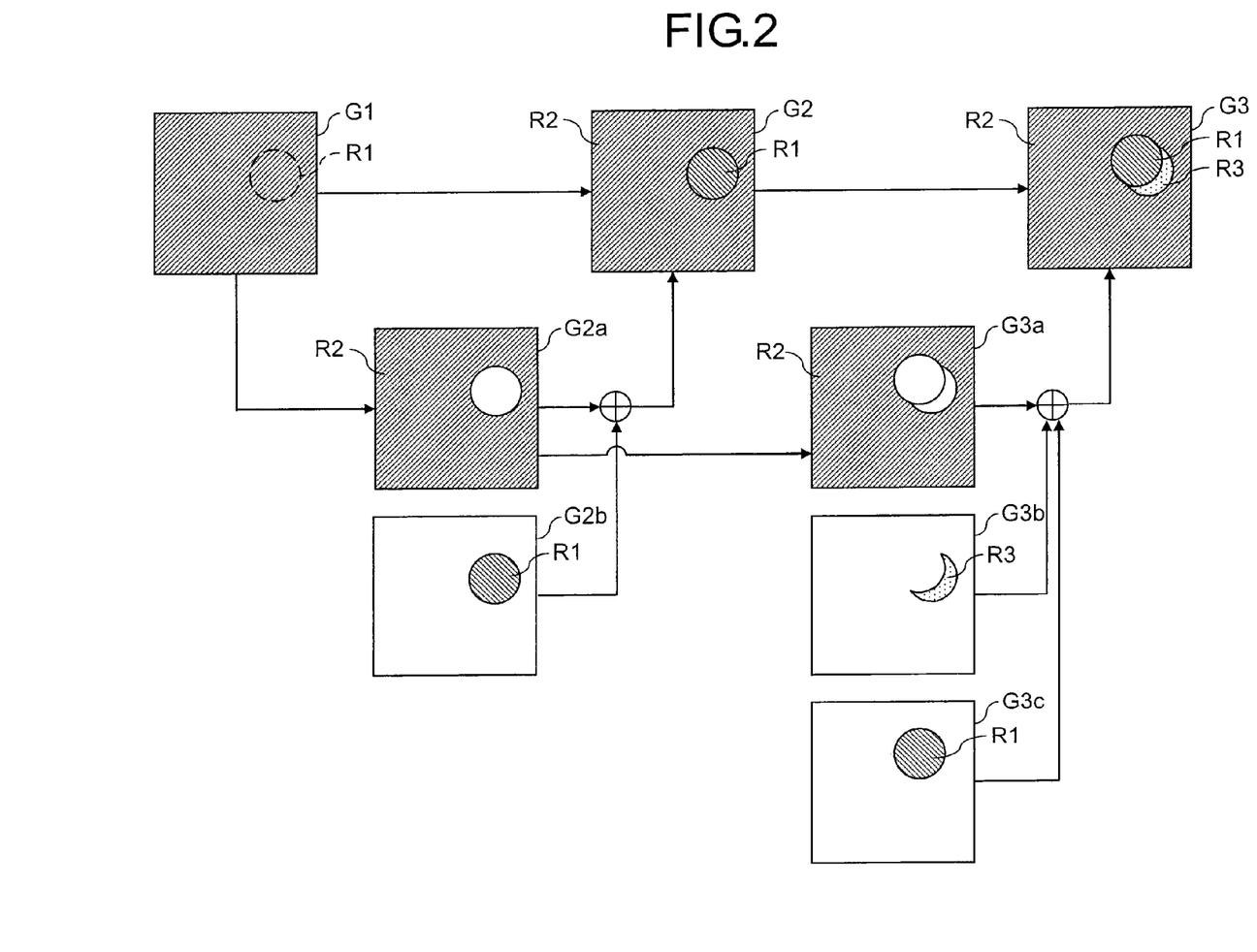
FIG. 2 is an explanatory diagram for explaining an image synthesizing process of an image processing device included in the X-ray image diagnosis apparatus shown in FIG. 1.

As shown in FIG. 2, once a region of interest R1 is set in an X-ray image (original image) G1 of the entire X-ray irradiation field, the image processing device 5 uses the image processing unit 5b to create an X-ray image G2a of a peripheral region R2 excluding the region of interest R1 in the entire X-ray irradiation field, from the X-ray image G1 stored in the image storage unit 5c. The X-ray image G2a of the peripheral region R2 and an X-ray image G2b of the region of interest R1 are then synthesized to create a synthesized image G2. This synthesized image G2 is displayed on the display unit 6.

Thereafter, the fluoroscopy (X-ray imaging) is repeated only on the region of interest R1. As a result, only the X-ray image G2b of the region of interest R1 is updated and thus appears as a moving image, whereas the X-ray image G2a of the peripheral region R2 remains the same and thus appears as a still image. As will be used in a subsequent process, this synthesized image G2 is stored in the image storage unit 5c.

Here, in the setting of the region of interest R1 mentioned above, the operator operates the mouse and/or the like in the operation unit 7d to specify, for example, a target part showing movement that is particularly important in diagnosis, as the region of interest R1 in the X-ray image G1 of the entire X-ray irradiation field displayed on the display unit 6. In response, the system control unit 7a sets the region of interest R1 and inputs information (e.g. coordinate information) on the region of interest R1 to the image processing device 5. The image processing device 5 uses that information to locate the region of interest R1, extracts the X-ray image G2a of the peripheral region R2 out of the X-ray image G1 stored in the image storage unit 5c, and synthesizes the X-ray image G2a and the X-ray image G2b of the region of interest R1.

Then, when the region of interest R1 mentioned above is changed, the image processing device 5 uses the image processing unit 5b to create an X-ray image G3a of the peripheral region R2 excluding the region of interest R1 before and after the change in the entire X-ray irradiation field, from the X-ray image G2a of the peripheral region R2 stored in the image storage unit 5c. Further, the image processing device 5 creates an X-ray image G3b of a changed region R3 which is in the region of interest R1 before the change and is changed to the peripheral region R2, from the X-ray image G2b of the region of interest R1 stored in the image storage unit 5c. After this image creation, the image processing device 5 synthesizes the X-ray images G3a and G3b and an X-ray image G3c of the region of interest R1 after the change to create a synthesized image G3. This synthesized image G3 is displayed on the display unit 6.

Thereafter, the fluoroscopy (X-ray imaging) is repeated only on the region of interest R1 after the change. As a result, only the X-ray image G3c of the region of interest R1 after the change is updated and thus appears as a moving image, whereas the X-ray image G3a of the peripheral region R2 and the X-ray image G3b of the changed region R3 remain the same and thus appear as still images. Thus, the X-ray image G3b of the changed region R3 is synthesized as part of the peripheral region R2 only once immediately after the change of the region of interest R1. As will be used when the region of interest R1 is changed again, this synthesized image G3 is stored in the image storage unit 5c.

Next, an image synthesizing-displaying process performed by the X-ray image diagnosis apparatus 1 including the image processing device 5 will be described in detail.

Figure 3:
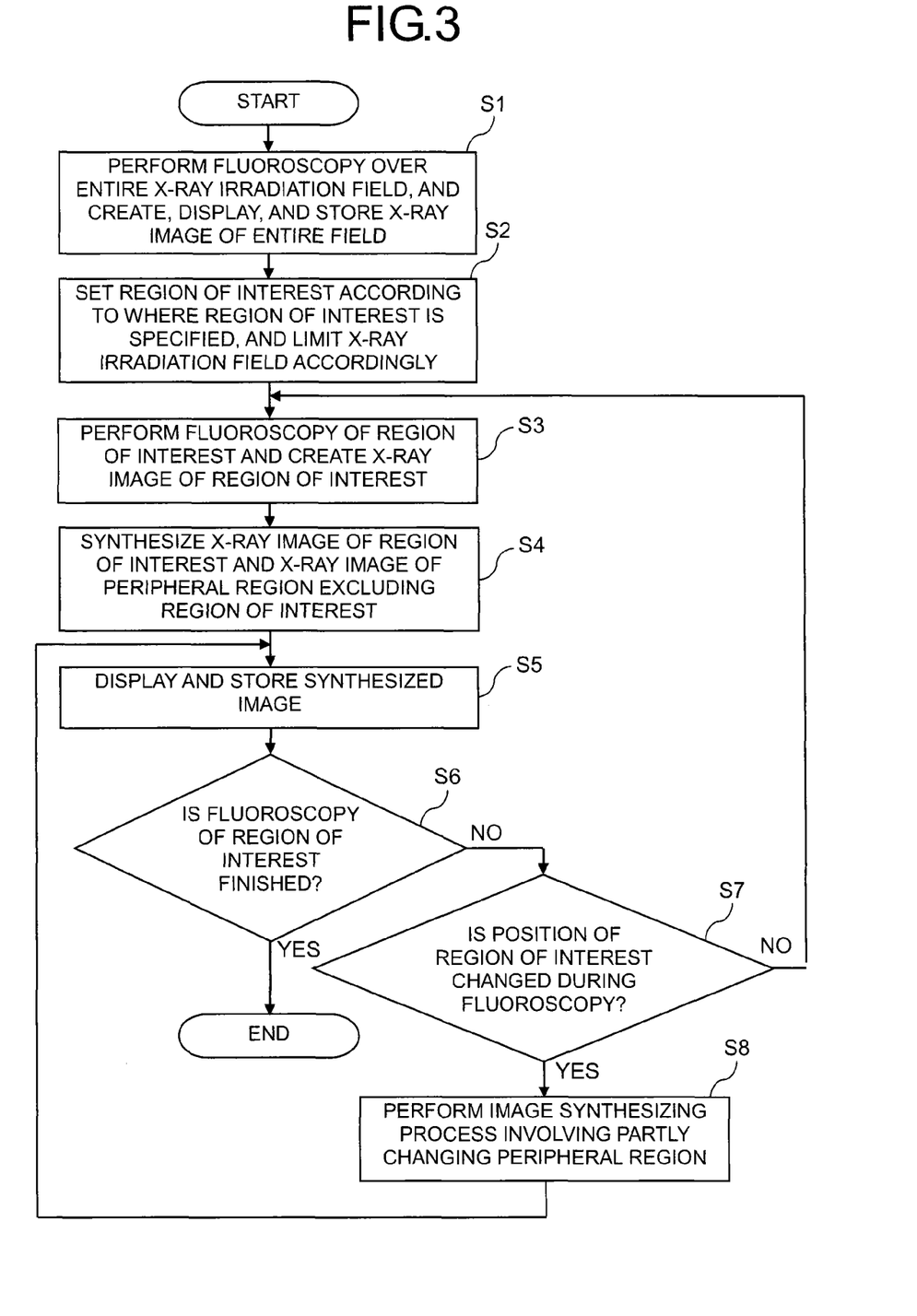
FIG. 3 is a flowchart showing the flow of an image synthesizing-displaying process performed by the X-ray image diagnosis apparatus shown in FIG. 1.

As shown in FIG. 3, first, fluoroscopy is performed over the entire X-ray irradiation field to create the X-ray image G1 of the entire field, and the X-ray image G1 is displayed and stored (step S1). Then, the region of interest R1 is set in accordance with where the region of interest R1 is specified, and the X-ray irradiation field is limited accordingly (step S2).

In step S1, the fluoroscopy is performed over the entire X-ray irradiation field which is adjusted to a predetermined X-ray irradiation field by adjusting the opening degree of the variable X-ray diaphragm 3a2 by means of the diaphragm-movement control unit 7b. The X-ray image signals obtained by the fluoroscopy are inputted to the image input unit 5a. The image processing unit 5b creates the X-ray image G1 of the entire field on the basis of the inputted X-ray image signals. The created X-ray image G1 is sent to the display unit 6 through the image output unit 5d to be displayed and also stored in the image storage unit 5c. Thereafter, the operator operates the mouse and/or the like in the operation unit 7d to specify, for example, a target part showing movement that is particularly important in diagnosis, as the region of interest R1 in the X-ray image G1 of the entire field displayed on the display unit 6.

In step S2, the system control unit 7a sets the region of interest R1 in accordance with where the region of interest R1 is specified, and outputs information (e.g. coordinate information) on the region of interest R1 to the image processing device 5 and the diaphragm-movement control unit 7b. The diaphragm-movement control unit 7b drives the variable X-ray diaphragm 3a2 in accordance with the position and size of the region of interest R1 included in that information so that the opening degree of the variable X-ray diaphragm 3a2 can be so adjusted as to provide an X-ray irradiation field that matches the position and size of the region of interest R1. Note that various publicly-known means can be used for the setting of the region of interest R1.

After step S2, fluoroscopy is performed on the region of interest R1 to create the X-ray image G2b of the region of interest R1 (step S3). Further, the X-ray image Gb2 of the region of interest R1 and the X-ray image G2a of the peripheral region R2 excluding the region of interest R1 are synthesized (step S4), and that synthesized image G2 is displayed and stored (step S5).

In step S3, the fluoroscopy (X-ray imaging) is performed only on the region of interest R1, and the X-ray image signals obtained by that fluoroscopy are inputted to the image input unit 5a. Based on the inputted X-ray image signals, the image processing unit 5b creates the X-ray image G2b of the region of interest R1.

In step S4, since the coordinate position of the region of interest R1 is known already, this coordinate data is used to extract the region of interest R1 out of the X-ray image G1 read out from the image storage unit 5c to create the X-ray image G2a of the peripheral region R2 excluding the region of interest R1. Then, the X-ray image G2a of the peripheral region R2 and the X-ray image G2b of the region of interest R1 are synthesized to create the synthesized image G2. This synthesized image G2 is stored in the image storage unit 5c, and is read out and used when necessary.

In step S5, the image output unit 5d outputs the created synthesized image G2 to the display unit 6, and the display unit 6 in turn displays the synthesized image G2. The synthesized image G2 is used by being viewed by a doctor, an assistant, etc.

After step S5, it is determined whether or not the fluoroscopy of the region of interest R1 is finished (step S6). The process ends if it is determined that the fluoroscopy of the region of interest R1 is finished (YES in step S6). On the other hand, if it is determined that the fluoroscopy of the region of interest R1 is not yet finished (NO in step S6), it is then determined whether or not the position of the region of interest R1 is changed during the fluoroscopy (step S7). The process returns to step S3 if it is determined that the position of the region of interest R1 is not changed (NO in step S7). On the other hand, if it is determined that the position of the region of interest R1 is changed (YES in step S7), the image synthesizing process involving partly changing the peripheral region is performed (step S8). The process then returns to step S5.

In step S6, the operator operates the mouse and/or the like in the operation unit 7d to issue an instruction to finish the fluoroscopy of the region of interest R1. In response, the system control unit 7a ends the fluoroscopic operation on the region of interest R1. Accordingly, the X-ray image G2b of the region of interest R1 in the synthesized image G2 stops being updated.

The process returns to step S3 if it is determined in step S7 that the position of the region of interest R1 is not changed. Thus, until the instruction to finish the fluoroscopy of the region of interest R1 is issued in step S6, the fluoroscopy of the region of interest R1 is performed to keep updating only the X-ray image G2b of the region of interest R1. Thereby, the X-ray image G2b of the region of interest R1 appears as a moving image. In this event, the X-ray image G2a of the peripheral region R2 remains the same and thus appears as a still image.

As described, when the region of interest R1 is set for the purpose of, for example, viewing a moving image of a target part, the peripheral region R2 outside the region of interest R1 is not irradiated with X rays, while only the region of interest R1 is irradiated with X rays, and the X-ray image G2b of the region of interest R1 is obtained. Then, the X-ray image G2a of the peripheral region R2 keeps being displayed as a still image in the periphery of the X-ray image G2b of the region of interest R1 being a moving image. This clearly shows the positional relationship between the moving image of the region of interest R1 and the still image of the peripheral region R2 and thereby makes the diagnosis easier. Further, since the still image of the peripheral region R2 is an image stored in the image storage unit 5c before the moving image is obtained, the periphery region R2 is not irradiated with X rays after the still image is stored. This reduces the exposure dose of the subject P accordingly.

Figure 4:
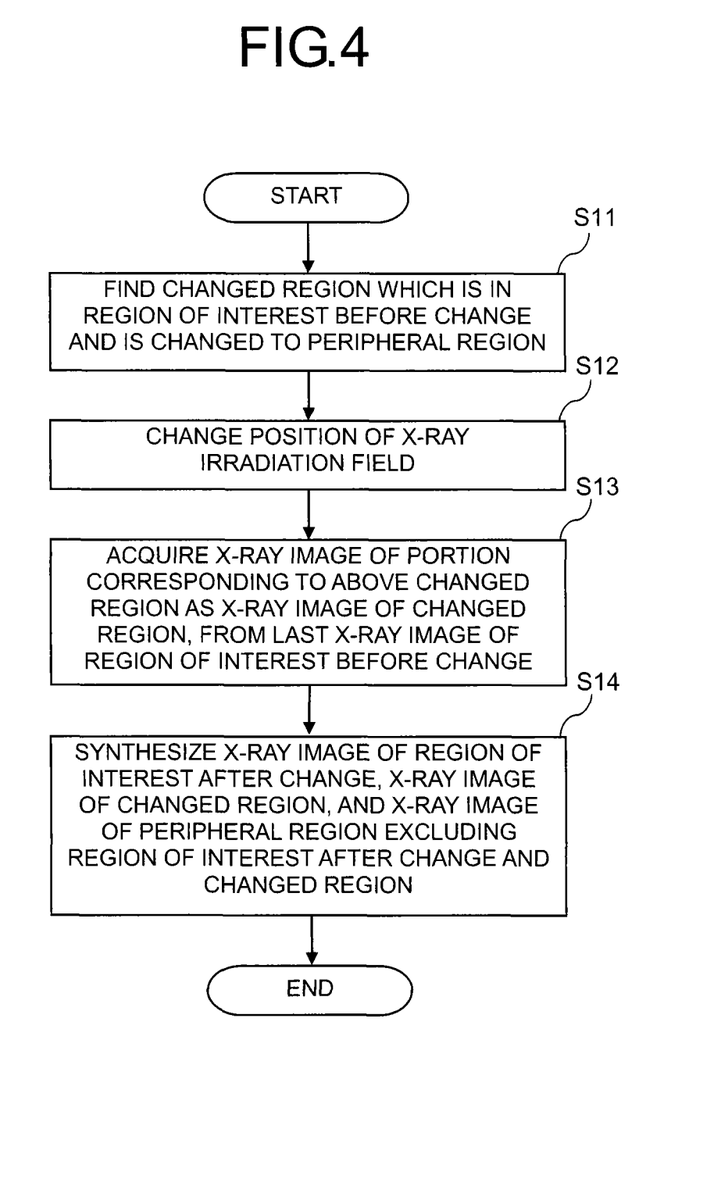
FIG. 4 is a flowchart showing the flow of an image synthesizing process in the image synthesizing-displaying process shown in FIG. 3 which involves partly changing a peripheral region.

In step S8, as shown in FIG. 4, the changed region R3 which is in the region of interest R1 before the change and is changed to the peripheral region R2 is obtained in response to a change in the region of interest R1 (step S11). The position of the X-ray irradiation field is changed in accordance with the region of interest R1 after the change (step S12). Then, an X-ray image of the changed region R3 is acquired as the X-ray image G3b of the changed region R3 from the last X-ray image G2b of the region of interest R1 before the change (step S13). The X-ray image G3c of the region of interest R1 after the change, the X-ray image G3b of the changed region R3, and the X-ray image G3a of the peripheral region R2 excluding the region of interest R1 before and after the change in the entire X-ray irradiation field are synthesized (step S14). After finishing step S8 as described above, the process returns to step S5, and the synthesized image G3 is displayed and stored.

Here, as for the pixels of the changed region R3 which is in the region of interest R1 before the change and is changed to the peripheral region R2, the image processing unit 5b holds X-ray detection values (pixel values) found in the last X-ray irradiation, and the pixels of the changed region R3 are updated to the last held X-ray irradiation values. Note that since the electrocardiograph 7e is connected, the image processing unit 5b may hold X-ray detection values found in the last X-ray irradiation that is synchronized with a particular phase in the electrocardiographic waveform (e.g. the end diastole, the end systole, or the like), instead of those found in a normal "last" irradiation.

As described, even when the region of interest R1 is changed, the X-ray image G3b of the changed region R3 is acquired from the X-ray image G2b of the region of interest R1 before the change and superimposed on the X-ray image G3a of the peripheral region R2, to thereby create the synthesized image G3 together with the X-ray image G3c of the region of interest R1 after the change. Thus, when the region of interest R1 is changed, the X-ray image G3b of the changed region R3 is updated using the X-ray image G2b of the region of interest R1 before the change and turns into part of the peripheral region R2. Accordingly, even when the region of interest R1 is changed, it is possible to accurately figure out the positional relationship between the moving image of the region of interest R1 and the still image of its peripheral region R2. Moreover, since the changed region R3 is updated, the X-ray image G1 stored in advance does not need to be updated, thereby eliminating the need for re-capturing an X-ray image of the entire X-ray irradiation field. This can prevent increase in the exposure dose due to the re-capturing of an X-ray image and also to prevent deterioration in operability.

Here, even when the region of interest R1 is changed and moved greatly, the fluoroscopy is performed at predetermined timings to capture the X-ray image G2b of the region of interest R1 continuously while the region of interest R1 is being moved. By using the X-ray image G2b of the region of interest R1 obtained sequentially by the continuous image capturing, the X-ray image G3b of the changed region R3 that moves along with the movement of the region of interest R1 are obtained sequentially. Thus, by repeating the updating process of the changed region R3 as described above, the moving changed region R3 can be updated sequentially. Accordingly, even when the region of interest R1 is changed and moved greatly, it is possible to accurately figure out the positional relationship between the moving image of the region of interest R1 and the still image of its peripheral region R2, as described above.

As has been described above, according to the first embodiment, when the region of interest R1 is changed, the X-ray image G3b of the changed region R3, which is in the region of interest R1 before the change and is changed to the peripheral region R2, is acquired from the X-ray image G2b of the region of interest R1 before the change and superimposed on the X-ray image G3a of the peripheral region R2, to thereby create the synthesized image G3 together with the X-ray image G3c of the region of interest R1 after the change. In this way, when the region of interest R1 is changed, the X-ray image G3b of the changed region R3 is also updated using the X-ray image G2b of the region of interest R1 before the change. Accordingly, while the exposure is reduced by limiting the X-ray irradiation field, it is also possible to accurately figure out the positional relationship between the region of interest R1 and its peripheral region R2 even when the region of interest R1 is changed. Further, since the changed region R3 is updated, the X-ray image G1 stored in advance does not need to be updated, thereby eliminating the need for re-capturing an X-ray image of the entire X-ray irradiation field. Accordingly, it is possible to prevent increase in the exposure dose due to the re-capturing of an X-ray image and deterioration in operability.

Moreover, an X-ray image of the region of interest R1 synchronized with the electrocardiographic waveform can be used as the X-ray image G2b of the region of interest R1 before its change. Thus, the X-ray image can be obtained in synchronization with movement of the target part. In this way, clear images can be used as the various images mentioned earlier, instead of using X-ray images with imaging defects such as blur. Accordingly, it is possible to more accurately figure out the positional relationship between the region of interest R1 and its peripheral region R2.

Specifically, an X-ray image can be obtained in synchronization with movement of the heart in a case of using an X-ray image of the region of interest R1 synchronized with the expansion or contraction of the heart in its electrocardiographic waveform. Alternatively, an X-ray image can be obtained in synchronization with movement of the lungs in a case of using an X-ray image of the region of interest R1 synchronized with the expansion or contraction of the lungs. Since the liver moves with the movement of the lungs, using an X-ray image of the region of interest R1 synchronized with the expansion or contraction of the lungs is effective when the target part is the liver. Even when the target part is a part as mentioned above that moves actively, clear X-ray images can still be used as the various images mentioned earlier. Accordingly, it is possible to more accurately figure out the positional relationship between the region of interest R1 and its peripheral region R2.

Second Embodiment

A second embodiment will be described with reference to FIG. 5.

The second embodiment is basically the same as the first embodiment. Thus, the second embodiment will only describe portions that are different from the first embodiment and omits description of the same portions as the portions described in the first embodiment.

Figure 5:
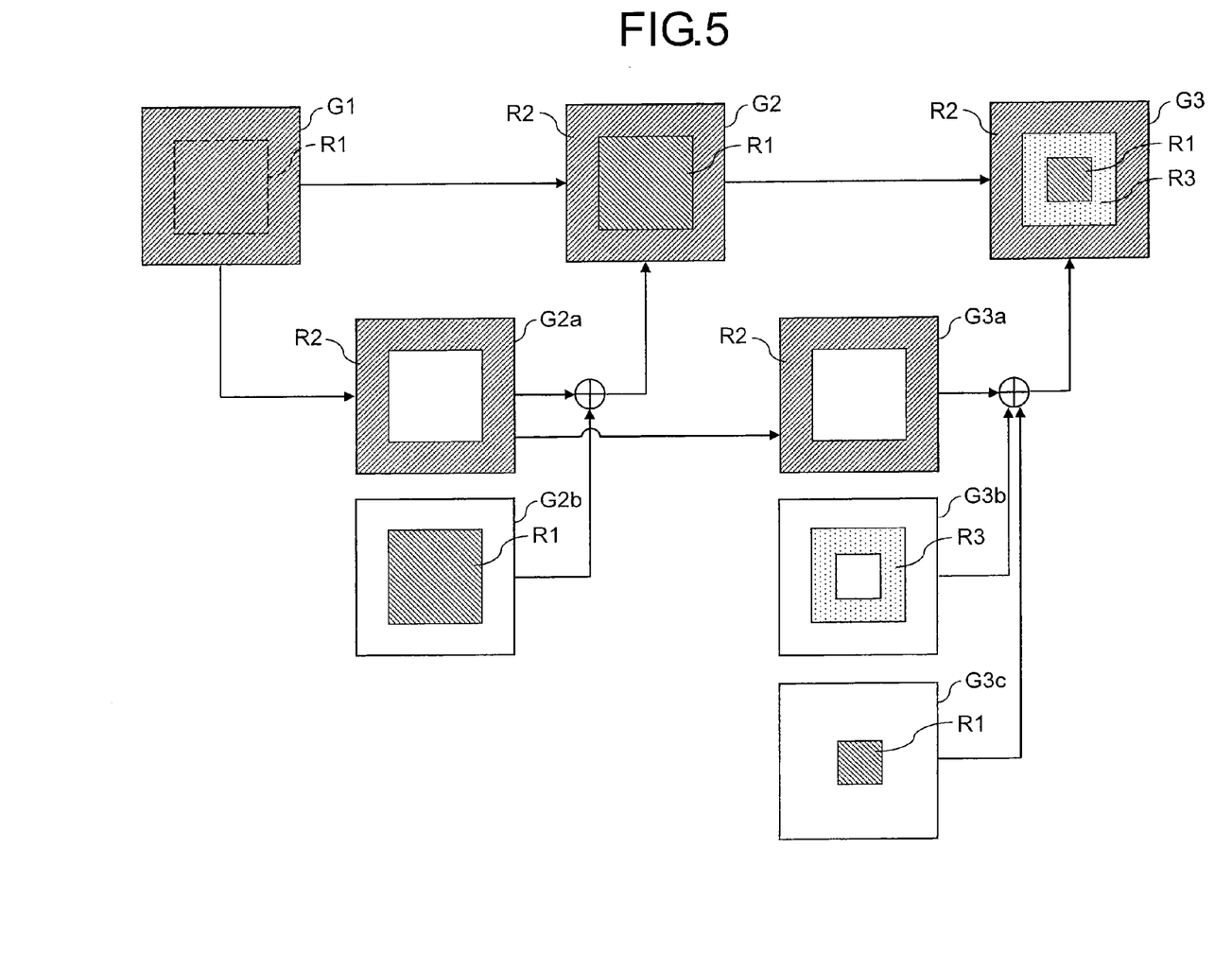
FIG. 5 is an explanatory diagram for explaining an image synthesizing process of an image processing device included in an X-ray image diagnosis apparatus according to a second embodiment.

As shown in FIG. 5, once a region of interest R1 is set in an X-ray image (original image) G1 of the entire X-ray irradiation field, the image processing device 5 uses the image processing unit 5b to create an X-ray image G2a of a peripheral region R2 excluding the region of interest R1 in the entire X-ray irradiation field, from the X-ray image G1 stored in the image storage unit 5c. The X-ray image G2a of the peripheral region R2 and an X-ray image G2b of the region of interest R1 are then synthesized to create a synthesized image G2. This synthesized image G2 is displayed on the display unit 6.

Thereafter, the fluoroscopy (X-ray imaging) is repeated only on the region of interest R1. As a result, only the X-ray image G2b of the region of interest R1 is updated and thus appears as a moving image, whereas the X-ray image G2a of the peripheral region R2 remains the same and thus appears as a still image. As will be used in a subsequent process, this synthesized image G2 is stored in the image storage unit 5c.

Here, in the setting of the region of interest R1 mentioned above, the operator operates the foot switch in the operation unit 7d to specify, for example, a target part showing movement that is particularly important in diagnosis, as the region of interest R1 in the X-ray image G1 of the entire field displayed on the display unit 6. In response, the system control unit 7a sets the region of interest R1 and inputs information (e.g. coordinate information) on the region of interest R1 to the image processing device 5. The image processing device 5 uses that information to locate the region of interest R1, extracts the X-ray image G2a of the peripheral region R2 out of the X-ray image G1 stored in the image storage unit 5c, and synthesizes the X-ray image G2a and the X-ray image G2b of the region of interest R1.

The operator further operates the foot switch in the operation unit 7d to specify a region of interest R1 which is smaller than the region of interest R1 mentioned above. In response, the system control unit 7a sets the region of interest R1 again. As a result, the region of interest R1 changes from a larger area to a smaller area. The size of the X-ray irradiation field can be switched among three different levels including the first level (entire X-ray irradiation field). That is, the size of the X-ray irradiation field satisfies a relationship of the first level (entire X-ray irradiation field)>the second level>the third level, and these levels can be switch from one another through the foot switch.

Then, when the region of interest R1 mentioned above is changed, the image processing device 5 uses the image processing unit 5b to create an X-ray image G3a of the peripheral region R2 excluding the region of interest R1 in the entire X-ray irradiation field, from the X-ray image G1 stored in the image storage unit 5c. Further, the image processing device 5 creates an X-ray image G3b of a changed region R3 which is in the region of interest R1 before the change and is changed to the peripheral region R2 (the difference between the region of interest R1 before the change and that after the change), from the X-ray image G2b of the region of interest R1 stored in the image storage unit 5c. After this image creation, the image processing device 5 synthesizes the X-ray images G3a and G3b and an X-ray image G3c of the region of interest R1 after the change to create a synthesized image G3. This synthesized image G3 is displayed on the display unit 6.

Thereafter, the fluoroscopy (X-ray imaging) is repeated only on the region of interest R1 after the change. As a result, only the X-ray image G3c of the region of interest R1 after the change is updated and thus appears as a moving image, whereas the X-ray image G3a of the peripheral region R2 and the X-ray image G3b of the changed region R3 remain the same and thus appear as still images. Thus, the X-ray image G3b of the changed region R3 is synthesized as part of the peripheral region R2 only once immediately after the change of the region of interest R1. As will be used when the region of interest R1 is changed again, this synthesized image G3 is stored in the image storage unit 5c.

The image synthesizing-displaying process performed by the X-ray image diagnosis apparatus 1 including the above-described image processing device 5 is the same as that in the first embodiment, except that the second embodiment determines in step S7 shown in FIG. 3 whether or not the size of the region of interest R1 is changed, instead of determining whether or not the position of the region of interest R1 is changed. Here, as described above, the operator operates the foot switch to switch the size of the region of interest R1 to any one of three different levels, for example. Similar advantageous effects as those of the first embodiment can be achieved even in a case of changing the size of the region of interest R1 as described above.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray image diagnosis apparatus comprising:
   an imaging unit, implemented by processing circuitry, configured to capture an X-ray image of a given region of a target part of a subject in a case of obtaining a still image of the target part, and to sequentially capture an X-ray image of a region of interest inside the given region in a case of obtaining a moving image of the target part;
   an image storage configured to store the X-ray image of the given region captured by the imaging unit;
   an image processing unit, implemented by the processing circuitry, configured to create a synthesized image by synthesizing the X-ray image of the region of interest captured by the imaging unit and an X-ray image of a peripheral region excluding the region of interest in the X-ray image of the given region stored in the image storage;
   a display configured to display the synthesized image created by the image processing unit;
   an X-ray diaphragm configured to focus X rays; and
   a control unit, implemented by the processing circuitry, configured to control the X-ray diaphragm to change the region of interest captured by the imaging unit from a first region of interest to a second region of interest, wherein
   when the region of interest is changed from the first region of interest to the second region of interest, the image processing unit creates the synthesized image by using an X-ray image of the second region of interest, an X-ray image of the first region of interest excluding an intersection between the second region of interest and the first region of interest, and an X-ray image of a peripheral region excluding a union between the first region of interest and the second region of interest.

2. The X-ray image diagnosis apparatus according to claim 1, wherein
   the image processing unit uses an X-ray image of the region of interest synchronized with an electrocardiographic waveform as the X-ray image of the first region of interest before the change.

3. The X-ray image diagnosis apparatus according to claim 2, wherein
   the image processing unit uses an X-ray image of the region of interest synchronized with any one of expansion and contraction of a heart in the electrocardiographic waveform as the X-ray image of the first region of interest.

4. The X-ray image diagnosis apparatus according to claim 1, wherein
   the image processing unit uses an X-ray image of the region of interest synchronized with any one of expansion and contraction of a lung as the X-ray image of the first region of interest.

* * * * *